(12) United States Patent
Baumgart

(10) Patent No.: US 9,730,662 B2
(45) Date of Patent: *Aug. 15, 2017

(54) SYSTEM AND METHOD FOR TRACKING BLOOD FLOW

(71) Applicant: Siemens Medical Solutions USA, Inc., Malvern, PA (US)

(72) Inventor: John Baumgart, Hoffman Estates, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 182 days.

This patent is subject to a terminal disclaimer.

(21) Appl. No.: 14/528,023

(22) Filed: Oct. 30, 2014

(65) Prior Publication Data

US 2015/0201894 A1 Jul. 23, 2015

Related U.S. Application Data

(60) Provisional application No. 61/928,560, filed on Jan. 17, 2014.

(51) Int. Cl.
*A61B 6/02* (2006.01)
*G06T 7/20* (2017.01)
(Continued)

(52) U.S. Cl.
CPC .............. *A61B 6/504* (2013.01); *A61B 6/481* (2013.01); *G06T 7/0016* (2013.01);
(Continued)

(58) Field of Classification Search
CPC ........... A61B 3/1241; A61B 6/00; A61B 6/02; A61B 6/48; A61B 6/481; A61B 6/50;
(Continued)

(56) References Cited

U.S. PATENT DOCUMENTS 4,504,908 A * 3/1985 Riederer ................ A61B 6/481
128/922
8,009,885 B2 * 8/2011 Grass .................... G06T 11/008
382/128

(Continued)

FOREIGN PATENT DOCUMENTS

JP WO 2013183775 A1 * 12/2013 ............. A61B 6/481

OTHER PUBLICATIONS

Schmitt, Hogler, et al., "Reconstruction of Blood Propagation in three-dimensional Rotational X-ray Angiography (3D-RA)", 2005, Computerized Medical Imaging and Graphics, vol. 29, pp. 507-520.*

(Continued)

*Primary Examiner* — Anastasia Midkiff

(57) ABSTRACT

A method and system for tracking blood flow within a vessel of a patient are presented. At least one or more medical images of the patient are acquired showing at least one vessel of the patient. A user marks a proximal point and a distal point on a vessel of interest on the medical images. The vessel of interest is tracked and corrections are made to the tracking using a tracking algorithm. A composite image is generated that encodes time to peak contrast agent intensity at each point of the vessel of interest as well as the intensity of the contrast at that time. A graph of time to peak contrast agent intensity versus distance from a proximal point of the vessel of interest is calculated and displayed to a user.

19 Claims, 5 Drawing Sheets
(1 of 5 Drawing Sheet(s) Filed in Color)

(51) Int. Cl.
*G06T 11/00* (2006.01)
*A61B 6/00* (2006.01)
*G06T 7/00* (2017.01)

(52) U.S. Cl.
CPC ............ *A61B 6/4441* (2013.01); *A61B 6/486* (2013.01); *A61B 6/507* (2013.01); *A61B 6/5217* (2013.01); *G06T 7/0014* (2013.01); *G06T 11/003* (2013.01); *G06T 2207/10076* (2013.01); *G06T 2207/20012* (2013.01); *G06T 2207/20101* (2013.01); *G06T 2207/20221* (2013.01); *G06T 2207/30104* (2013.01)

(58) Field of Classification Search
CPC ......... A61B 6/504; A61B 6/52; A61B 6/5211; A61B 6/5217; A61B 6/5252; A61B 6/5288; G06T 7/0012; G06T 7/0014; G06T 7/0016; G06T 7/20; G06T 7/2053; G06T 7/5086; G06T 11/00; G06T 11/003; G06T 11/008; G06T 2211/00; G06T 2211/40; G06T 2211/404; G06T 2207/00; G06T 2207/10; G06T 2207/10116; G06T 2207/10072; G06T 2207/10076; G06T 2207/10081; G06T 2207/20; G06T 2207/20008; G06T 2207/20012; G06T 2207/20092; G06T 2207/20101; G06T 2207/20104; G06T 2207/20144; G06T 2207/20221; G06T 2207/20212; G06T 2207/20224; G06T 2207/30; G06T 2207/30004; G06T 2207/30101; G06T 2207/30104; G06F 19/00; G06F 19/30; G06F 19/32; G06F 19/34
See application file for complete search history.

(56) References Cited

U.S. PATENT DOCUMENTS

| | | | |
|---|---|---|---|
| 8,050,474 | B2 | 11/2011 | Baumgart |
| 9,019,305 | B2* | 4/2015 | Baumgart ............ A61B 6/463 345/629 |
| 2010/0053209 | A1 | 3/2010 | Rauch et al. |
| 2010/0259550 | A1 | 10/2010 | Baumgart et al. |
| 2010/0305454 | A1* | 12/2010 | Dvorsky ............ A61B 5/0059 600/476 |
| 2011/0150309 | A1* | 6/2011 | Barfett ................ G06T 7/0028 382/131 |
| 2012/0099768 | A1* | 4/2012 | Helm ................ A61B 6/4405 382/128 |
| 2015/0071520 | A1* | 3/2015 | Takemoto ............ A61B 6/481 382/132 |

OTHER PUBLICATIONS

Shpilfoygel, Simon D., et al., "X-ray Videodensitometric Methods for Blood Flow and Velocity Measurement: A Critical Review of Literature", Sep. 2000, Med. Phys., vol. 27, No. 9, pp. 2008-2023.*
Kohler, T., et al., "Method for Flow Reconstruction from Dynamic X-ray Projection Measurements", Nuclear Science Symposium Conference Record, 2004 IEEE, vol. 5, pp. 3295-3298.*

* cited by examiner

SYSTEM AND METHOD FOR TRACKING BLOOD FLOW

CROSS REFERENCE TO RELATED APPLICATIONS

This application claims benefit of provisional patent application 61/928,560 filed Jan. 17, 2014, the entire content of which is hereby incorporated by reference.

FIELD

Aspects of the present invention relate to a system and a method for tracking a blood flow, and in particular, a system and a method for tracking a blood flow within a vessel of a patient in medical images.

BACKGROUND

The field of medical imaging has seen significant advances since the time X-rays were first used to determine anatomical abnormalities. Large amounts of image data can be generated by modern medical scanners and there remains a need for developing image processing techniques that can automate some or all of the processes to more quickly and effectively determine a presence of anatomical abnormalities in scanned medical images.

In angiographic X-ray imaging, contrast medium is used to enhance the contrast of blood-carrying structures within patient anatomy. For example, contrast medium is introduced into a patient volume (e.g., via intravenous injection) and an X-ray image of the volume is acquired while the medium is located within the volume. In the X-ray image, structures which contain the medium appear darker than they would otherwise appear.

In DSA (Digital Subtraction Angiography), a "mask image" of the patient volume is subtracted from an X-ray image acquired as described above. The mask image is acquired without the presence of the contrast medium and represents background anatomic detail. The resulting image is intended to portray only the vessel and perfuse tissue components of the patient volume which include contrast medium.

Digital medical images are constructed using raw image data obtained in an X-ray and as derived from, for example, the DSA. The digital medical images are typically either a two-dimensional ("2-D") image made of pixel elements or a three-dimensional ("3-D") image made of volume elements ("voxels"). Such 2-D or 3-D images are processed using medical image recognition techniques to determine the presence of anatomical structures, and as for example in a DSA, the flow of contrast agent through vessels of the patient.

With regards to the imaging of patient vessels and understanding the flow of blood through these vessels, current tools for analyzing blood flow present overall flow information for an entire image or a user-selected region. In cases where treatment of occlusions of specific vessels needs to be analysed, analysis of more than those specific vessels, being those in an entire image or selected region, can give a misleading picture of the effectiveness of treatment. Thus, there is a need for improved automated or semi-automated systems and methods for tracking and visualizing rate of blood flow through a tracked vessel.

SUMMARY

Briefly described, aspects of the present invention relate to a system and a method for tracking a blood flow, and in particular, a system and a method for tracking a blood flow within a vessel of a patient in medical images.

According to a first embodiment, a method for tracking a blood flow within a vessel of a patient is provided. The method comprises acquiring at least one or more medical images of the patient using an imaging system. The at least one or more medical images may show at least one vessel of the patient. A vessel of interest may be identified on the acquired one or more medical images. The vessel of interest may be tracked. A composite image of the patient may be generated from the acquired one or more medical images. The composite image may comprise a time to peak contrast agent intensity at a point on the vessel of interest. A graph comprising the time to peak contrast agent intensity at the point on the vessel of interest versus a distance of the point along the vessel of interest maybe calculated.

According to a second embodiment, a system for tracking a blood flow within a vessel of a patient is provided. The system may comprise an imaging system for acquiring one or more medical images of the patient. The one or more medical images may comprise at least one vessel of the patient. The system may further comprise a control and processing system. The control and processing system is configured to identify a vessel of interest on the acquired one or more medical images, to track the vessel of interest, to generate a composite image from the acquired one or more medical images. The composite image may comprise a time to peak contrast agent intensity at a point on the vessel of interest. The control and processing system is further configured to calculate a graph comprising the time to peak contrast agent intensity at the point on the vessel of interest versus a distance of the point along the vessel of interest.

According to a third embodiment, a non-transitory computer readable storage device comprising a computer program is provided. The computer program when is executed by a computer performs method steps comprising identifying a vessel of interest of a patient on one or more medical images of the patient. The one or more medical images of the patient may be acquired using an imaging system. The one or more medical images of the patient may comprise at least one vessel of the patient. The method steps further comprise tracking the vessel of interest, generating a composite image from the acquired one or more medical images. The composite image may comprise a time to peak contrast agent intensity at a point on the vessel of interest. The method steps further comprise calculating a graph comprising the time to peak contrast agent intensity at the point on the vessel of interest versus a distance of the point along the vessel of interest.

Various aspects and embodiments of the application as described above and hereinafter may not only be used in the combinations explicitly described, but also in other combinations. Modifications may occur and be understood to the skilled person upon reading the description.

BRIEF DESCRIPTION OF THE DRAWINGS

The patent or application filed contains at least one drawing executed in color. Copies of this patent or patent application publication with color drawing(s) will be provided by the Office upon request and payment of the necessary fee.

A more complete appreciation of the present disclosure and many of the attendant aspects thereof will be readily obtained as the same becomes better understood by reference to the following detailed description when considered in connection with the accompanying drawings. In the drawings.

To facilitate understanding, identical reference numerals have been used, where possible, to designate identical elements that are common to the figures.

DETAILED DESCRIPTION OF INVENTION

Figure 1:
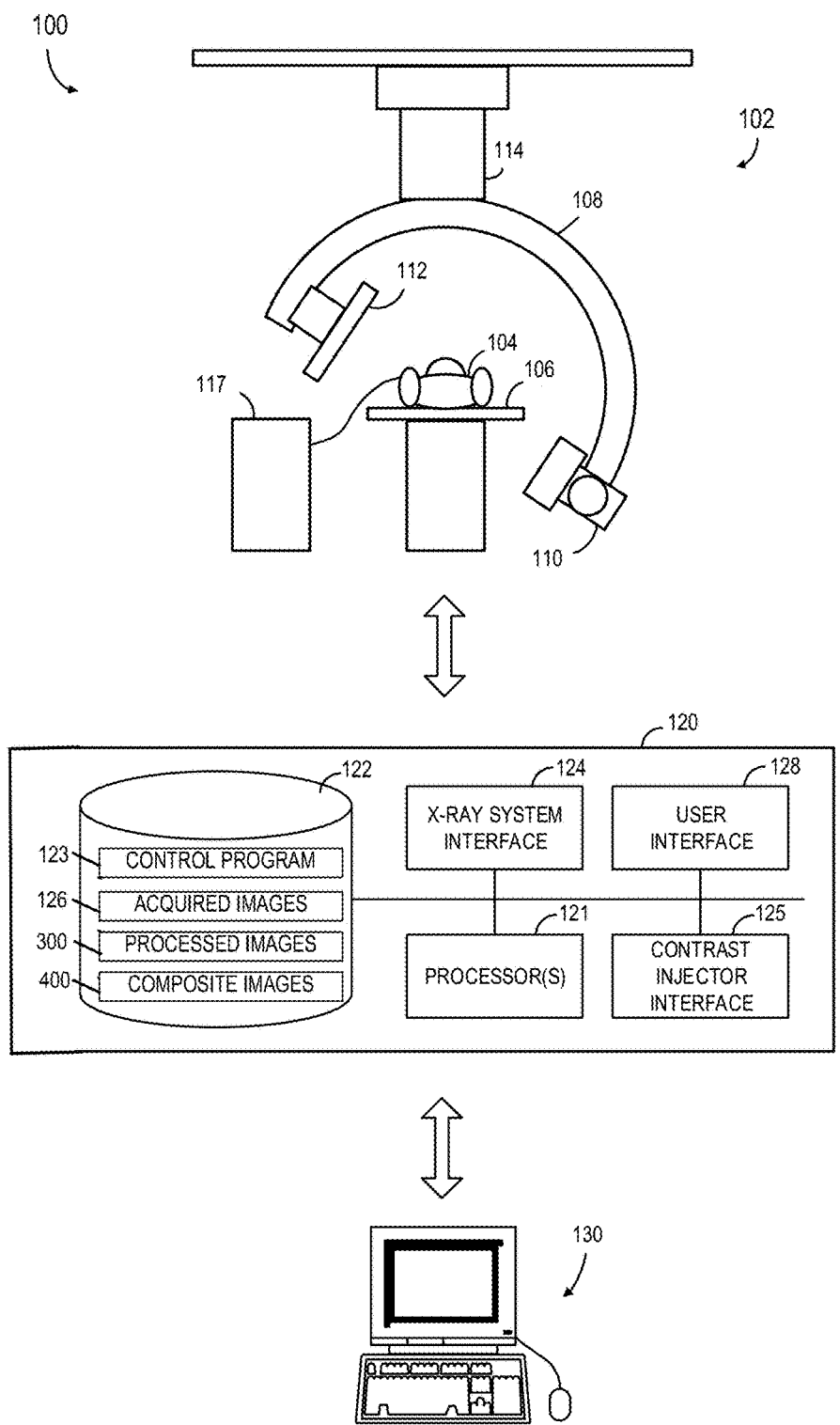
FIG. 1 is an illustration showing an exemplary X-ray imaging system for acquiring angiographic X-ray images for use with embodiments disclosed herein.

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

The term "X-ray image" as used herein may mean a visible X-ray image (e.g., displayed on a video screen) or a digital representation of an X-ray image (e.g., a file corresponding to the pixel output of an X-ray detector). The term "in-treatment X-ray image" as used herein may refer to images captured at any point in time during a treatment delivery phase of a radiosurgery or radiotherapy procedure, which may include times when the radiation source is either on or off. From time to time, for convenience of description, angiographic X-ray imaging data may be used herein as an exemplary imaging format. It will be appreciated, however, that data from any type of imaging system including but not limited to X-ray radiographs, MRI, CT, PET (positron emission tomography), PET-CT, SPECT, SPECT-CT, MR-PET, 3D ultrasound images or the like may also be used in various embodiments of the invention.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, a control and processing system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

As used herein, the term "image" refers to multi-dimensional data composed of discrete image elements (e.g., pixels for 2-D images and voxels for 3-D images). The image may be, for example, a medical image of a subject collected by angiographic X-ray, computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R or $R^7$, the methods of the inventions are not limited to such images, and can be applied to images of any dimension, e.g., a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

FIG. 1 illustrates an exemplary imaging system 100 for use with embodiments disclosed herein. System 100 includes an X-ray imaging system 102 for acquiring angiographic X-ray images, a control and processing system 120, and an operator terminal 130. Generally, according to preferred embodiments, the X-ray imaging system 102 introduces contrast medium into a patient volume and acquires X-ray images of the patient volume. The control and processing system 120 controls the X-ray imaging system 102 and receives the acquired images therefrom. The control and processing system 120 processes the images as described below and provides the processed images to a terminal 130 for display. Such processing may be based on user input received by the terminal 130 and provided to the control and processing system 120 by terminal 130.

X-ray imaging system 102 comprises a C-arm 108 on which a radiation source 110 and a radiation detector 112 are mounted. The C-arm 108 is mounted on a support 114 and is configured to translate clockwise or counter-clockwise with respect to support 114. This translation rotates the radiation source 110 and the radiation detector 112 around a central volume while maintaining the physical relationship there between. Embodiments are not limited to C-arm-based imaging systems.

The radiation source 110 may comprise any suitable radiation source, X-ray tube. In some embodiments, the radiation source 110 emits electron, photon, or other type of radiation having energies ranging from 50 to 150 keV.

The radiation detector 112 may comprise any system to acquire an image based on received X-ray radiation. In some embodiments, the radiation detector 112 is a flat-panel imaging device using a scintillator layer and solid-state amorphous silicon photodiodes deployed in a two-dimensional array. The scintillator layer receives photons and generates light in proportion to the intensity of the received photons. The array of photodiodes receives the light and records the intensity of received light as stored electrical charge.

In other embodiments, the radiation detector 112 converts received photons to electrical charge without requiring a scintillator layer. The photons are absorbed directly by an array of amorphous selenium photoconductors. The photoconductors convert the photons directly to stored electrical charge. The radiation detector 112 may comprise a CCD or tube-based camera, including a light-proof housing within which are disposed a scintillator, a mirror, and a camera.

The charge developed and stored by the radiation detector 112 represents radiation intensities at each location of a radiation field produced by X-rays emitted from the radiation source 110. The radiation intensity at a particular location of the radiation field represents the attenuated properties of tissues lying along a divergent line between the radiation source 110 and the particular location of the radiation field.

A contrast medium injector 117 may comprise any known device or devices suitable to controllably introduce contrast medium into a volume of patient 104. As described above, volumes which contain contrast medium appear darker in X-ray images than they would otherwise appear. The contrast medium injector 117 may include a reservoir for each of one or more contrast media, and a patient interface such as medical-grade tubing terminating in a hollow needle.

The control and processing system 120 may comprise any general-purpose or dedicated computing system. Accordingly, the control and processing system 120 may include one or more processors 121 configured to execute processor-executable program code to cause the control and processing system 120 to operate as described herein, and a storage device 122 for storing the program code. The storage device 122 may comprise one or more fixed disks, solid-state random access memory, and/or removable media (e.g., a thumb drive) mounted in a corresponding interface (e.g., a USB port).

It is to be appreciated that at least a portion of the components shown in the control and processing system 120 of FIG. 1 may be implemented in various forms of hardware, software or combinations thereof, e.g., one or more digital signal processors with associated memory, application-specific integrated circuits, functional circuitry, etc. It should also be noted that some or all of the system 120, for example, can be incorporated in an application specific or general-use integrated circuit. For example, one or more method steps described below with respect to FIG. 2, or elsewhere, could be implemented in hardware in an application specific integrated circuit (ASIC) rather than using software.

The storage device 122 stores program code of a system control program 123. One or more processors 121 may execute the system control program 123 to, for example, move the C-arm 108, to cause the radiation source 110 to emit radiation, to control the detector 112 to acquire an image, to cause the injector 117 to introduce contrast medium into a volume of patient 104, and to perform any other function. In this regard, the system 120 may include an X-ray system interface 124 and a contrast injector interface 125 for communication with the system 102.

Images acquired from the system 102 may be stored in the data storage device 122 as acquired images 126, in DICOM or another data format. Each acquired image 126 may be further associated with details of its acquisition, including but not limited to imaging plane position and angle, imaging position, radiation source-to-detector distance, patient anatomy imaged, patient position, contrast medium bolus injection profile, X-ray tube voltage, image resolution and radiation dosage.

Processor(s) 121 may execute the system control program 123 to process acquired images 126, resulting in one or more processed images 300. The user interface 128 may also receive input from the terminal 130, which is used to control processing of acquired images 126 as described below. Processed images 300 may be stored in the storage device 122 of the control and processing system 120. As further described below, composite image 400, constructed of one or more processed images 300, may also be stored in storage device 122.

The terminal 130 may simply comprise a display device and an input device coupled to the system 120. Some or all of the acquired images 126, processed images 300, and/or composite images 400 may be provided to the terminal 130 via a user interface 128 of system 120. The terminal 130 displays images received from the system 120 and receive user input which may be transmitted to the system 120 and used thereby to generate, modify or markup images for subsequent display by the terminal 130. In some embodiments the terminal 130 is a separate computing device such as, but not limited to, a desktop computer, a lap-top computer, a tablet computer, and a smartphone. The control and processing system 120 may be fully or partially integrated with terminal 130. In other embodiments, all or some of the control and processing system 120 may be in communication with the terminal 130 by wired link or wirelessly. More than one terminal 130 also may exist and located in for example the same room as patient 104 on table 106, an adjacent or nearby room, or in any other location.

Each of the imaging system 102, the control and processing system 120 and the terminal 130 may include other elements which are necessary for the operation thereof, as well as additional elements for providing functions other than those described herein.

According to the illustrated embodiment, the control and processing system 120 controls the elements of the X-ray imaging system 102. The control and processing system 120 also processes images received from the X-ray imaging system 102. Moreover, the system 120 receives input from the terminal 130 and provides processed images to the terminal 130. Embodiments are not limited to a single system performing each of these functions. For example, X-ray imaging system 102 may be controlled by a dedicated control system, with the acquired images being provided to a separate imaging processing system over a computer network or via a physical storage medium (e.g., a DVD).

Figure 2:
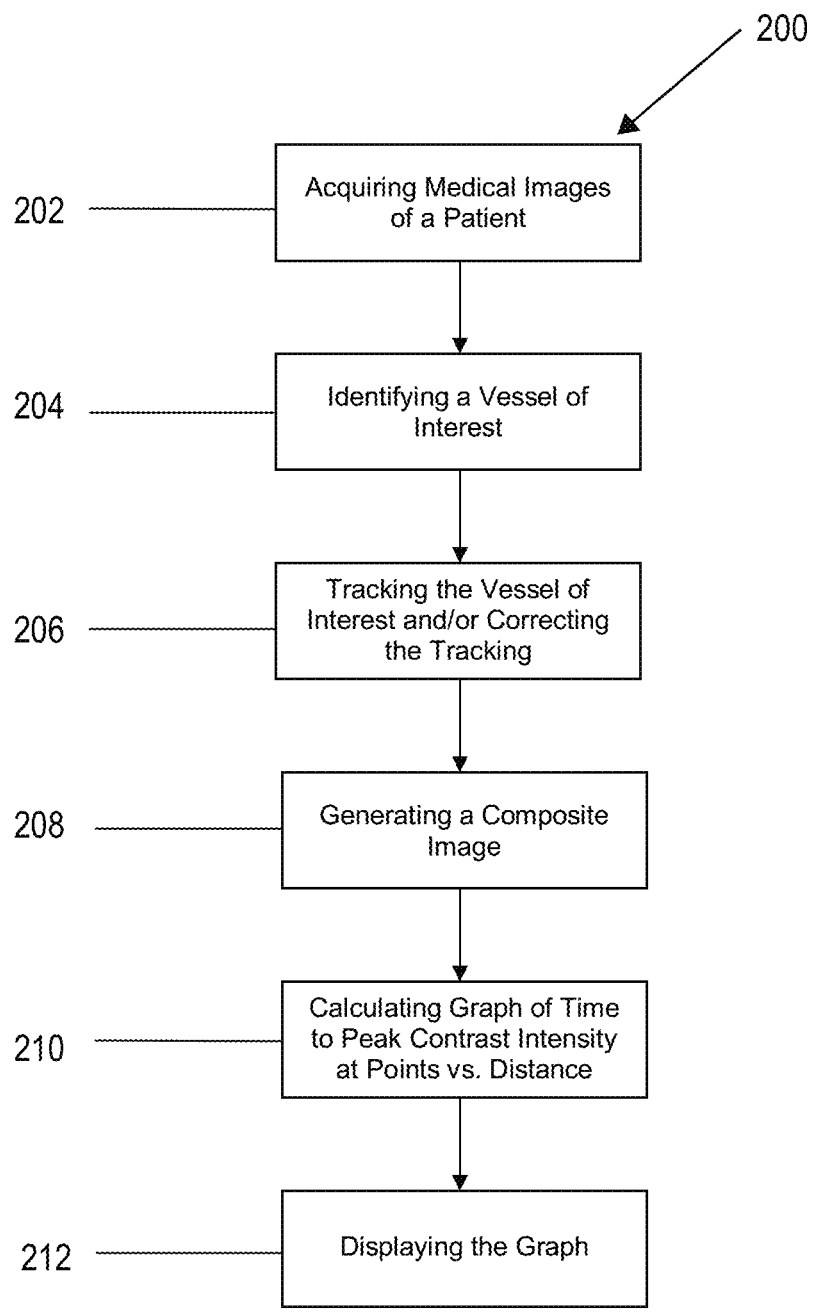
FIG. 2 is a flow diagram illustrating an exemplary workflow for tracking blood flow within a vessel of a patient according to an embodiments disclosed herein.

FIG. 2 is a flow diagram 200 illustrating an exemplary workflow for tracking blood flow within a vessel of a patient according to embodiments disclosed herein. According to the exemplary embodiment illustrated in FIG. 2, at least one or more acquired medical images 126 of a patient 104 may be acquired using the imaging system 102 at step 202. The at least one or more acquired medical images 126 may show at least one vessel of the patient 104. The imaging system 102 may comprise any type of imaging system including but not limited to X-ray radiographs, MRI, CT, PET (positron emission tomography), PET-CT, SPECT, SPECT-CT, MR-PET, 3D ultrasound images or the like may also be used in various embodiments of the invention. For illustration purpose, the preferred embodiment demonstrates the one or more acquired medical images 126 may be acquired by angiographic X-ray as shown by the X-ray imaging system 102 in FIG. 1.

According to an embodiment, a contrast agent may be injected into the patient 104, lying on patient table 106, using a contrast agent injector 117. The flow rate, volume, and/or location of the contrast agent may be controlled by a user, via input through the contrast injector interface 125, or automatically by the control and processing system 120. As the agent is introduced into the patient 104, the control and processing system 120 may instruct the X-ray imaging system 102 to acquire images of the vessels in the presence of the contrast agent. The control and processing system 120, and in particular the one or more processor(s) 121, may perform DSA on the acquired images 126 resulting in processed images 300.

Figure 3:
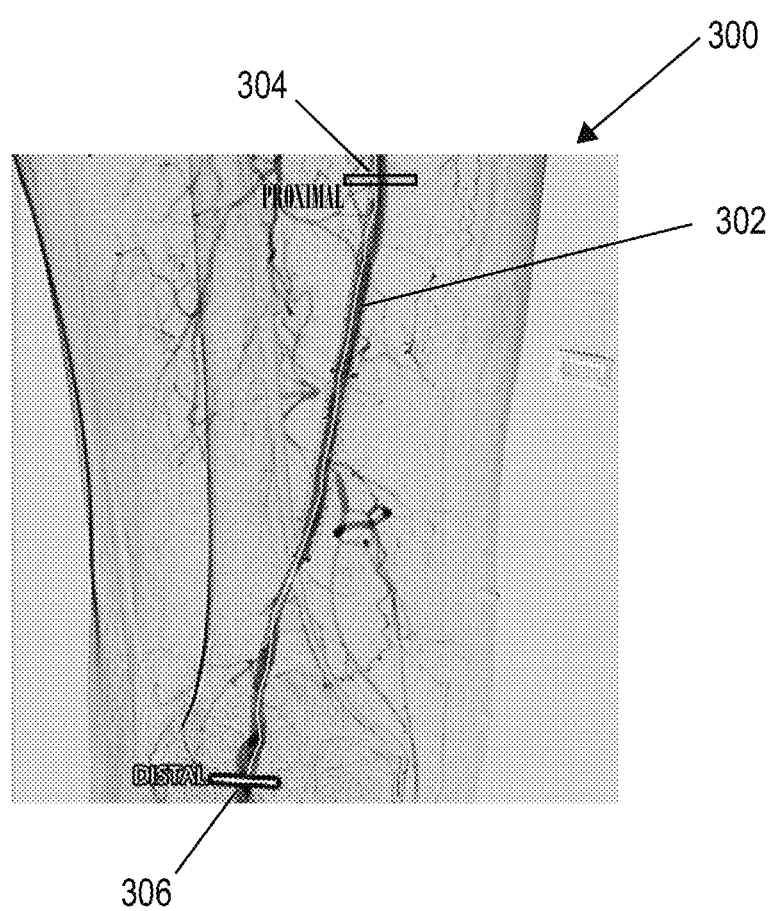
FIG. 3 is an exemplary angiographic X-ray image of a patient illustrating a vessel of interest to be tracked comprising a proximal point and a distal point according to embodiments disclosed herein.

Referring again to FIG. 2 as shown at step 204, a vessel of interest 302 may be identified in the processed medical images 300 (see also FIG. 3). The identification may be implemented by user selection, as for example, through the user interface 128. In some embodiments, the control and processing system 120, and in particular the one or more processor(s) 121, may automatically identify the vessel of interest 302 or provide the user with a series of identified vessel options so that the user may select a particular vessel as the vessel of interest 302.

According to an embodiment, the vessel of interest 302 may be identified in the processed medical images 300 by marking points on the vessel of interest 302. With the vessel identified, the one or more processor(s) 121 may select marking points on the vessel automatically. However it may be preferred that a user may manually mark points on the vessel of interest 302. The marking points of the vessel by the user may be achieved through terminal 130 by identifying points on the vessel of interest 302 with a computer mouse and then 'clicking' the particular area or perhaps by using a touch-screen interface and simply selecting marks with a finger for example. According to an embodiment, a user may mark a proximal point 304 on the vessel of interest 302 and/or a distal point 306 on the vessel of interest 302, referring to FIG. 3, which then may be tracked in the processed medical images 300. The one or more processor(s) 121 may then display the marked portions 304 and 306 of the vessel of interest 302 on a screen display at terminal 130.

FIG. 3 is an exemplary medical X-ray image 300 of a patient 104 illustrating a vessel of interest 302 to be tracked comprising a proximal point 304 and a distal point 306 according to embodiments disclosed herein. As illustrated in FIG. 3, a vessel of interest 302 is identified on the angiographic X-ray image 300. The vessel of interest 302 may be identified by a proximal point 304 and a distal point 306.

Referring again to FIG. 2 as shown at step 206, the vessel of interest 302 may be tracked by processor(s) 121. The processor 121 may need to make necessary corrections when tracking the vessel of interest 302. According to an embodiment, the tracking and/or corrections may be implemented by the processor 121 using a known algorithm, such as model-based algorithm or vector-based growing algorithm. In some embodiments, the tracking and/or corrections may be implemented by marking points on the vessel of interest 302. The tracking and/or corrections may be automatically implemented by the processor 121.

As shown in step 208 of FIG. 2, a composite image 400 of the patient 104 may be generated using the medical images 300. The composite image 400 may be encoded by the processor(s) 121 with a time to peak contrast agent intensity at a point on the vessel of interest 302. The composite image 400 may be encoded with a value of the peak contrast agent intensity, at that time, at the point on the vessel of interest 302. The composite image 400 may be stored in the storage device 122 of control and processing system 120.

Figure 4:
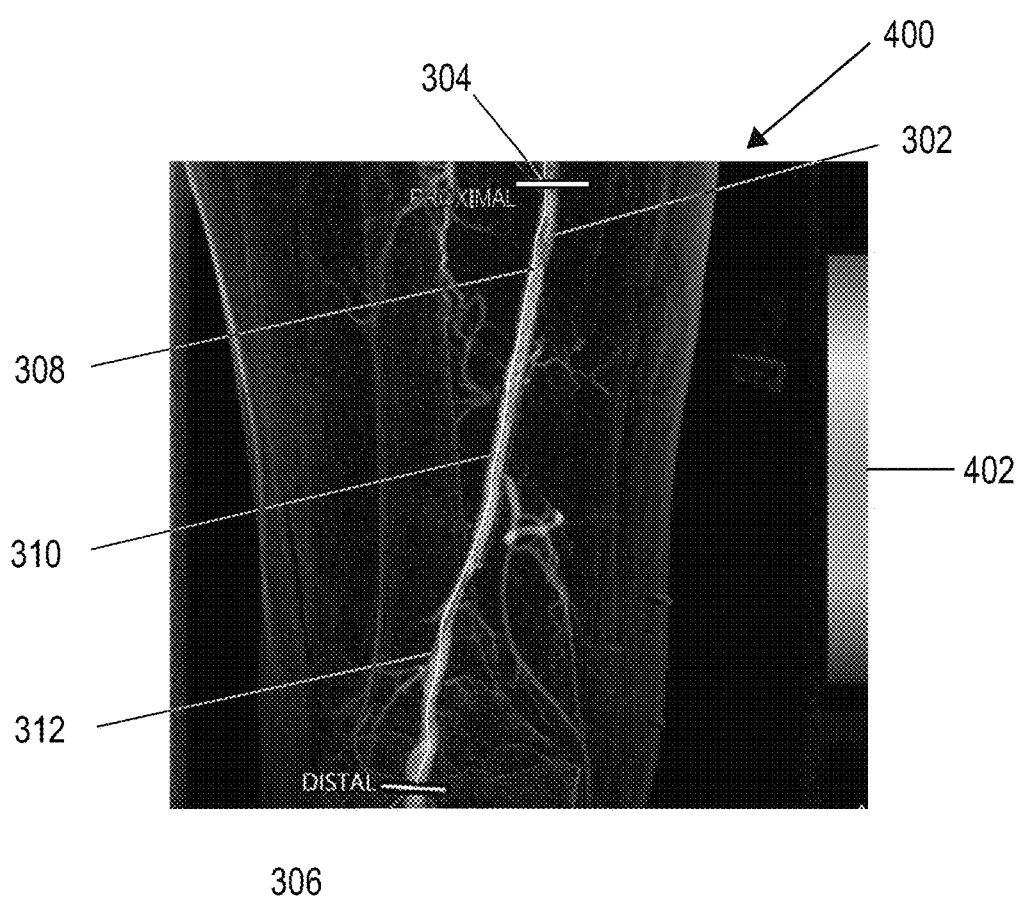
FIG. 4 is an exemplary composite image of a patient comprising encoded time and contrast agent intensity information on the vessel of interest to be tracked according to embodiments disclosed herein.

FIG. 4 is an exemplary composite image 400 of the patient 104 comprising encoded time and contrast agent intensity information on the vessel of interest 302 to be tracked according to embodiments disclosed herein. As illustrated in FIG. 4, the composite image 400 shows a vessel of interest 302 with a proximal point 304 and a distal point 306. A plurality of points may be marked along the vessel of interest 302, such as points 308, 310, and 312, as illustrated in FIG. 4. The points may be manually marked by a user or automatically marked by the processor(s) 121. The composite image 400 may be encoded with a time to peak contrast agent intensity at points 308, 310, 312, or any other points along the vessel of interest 302. The composite image 400 may be encoded with a value of the peak contrast agent intensity at that time on the points of the vessel of interest 302. According to an embodiment shown in FIG. 4, contrast agent flow information comprising time to peak contrast agent intensity at points on the vessel of interest 302 and/or a value of the peak contrast agent intensity at that time on the points may be illustrated by a color spectrum 402. For example, the peak contrast intensity may be identified by a 'red' color to illustrate the earliest time to peak in particular portions of the vessel, the peak contrast intensity may be identified by a 'blue' color to illustrate the latest time to peak in particular portions of the vessel, the peak contrast intensity may be identified by a 'green' color to illustrate the time between the earliest and the latest to peak in particular portions of the vessel.

Referring again to FIG. 2, a graph 500 illustrating time to peak contrast agent intensity at points on a vessel of interest 302 versus distance of the points along the vessel of interest 302 from a proximal point 304 of the vessel of interest 302 may be calculated by the processor(s) 121, at step 210, and displayed to a user on terminal 130 at step 212. In some embodiments, the graph 500 may illustrates time to peak contrast agent intensity at points on a vessel of interest 302 versus distance of the points along the vessel of interest 302 from a proximal point 304 of the vessel of interest 302 to a distal point 306 of the vessel of interest 302.

Figure 5:
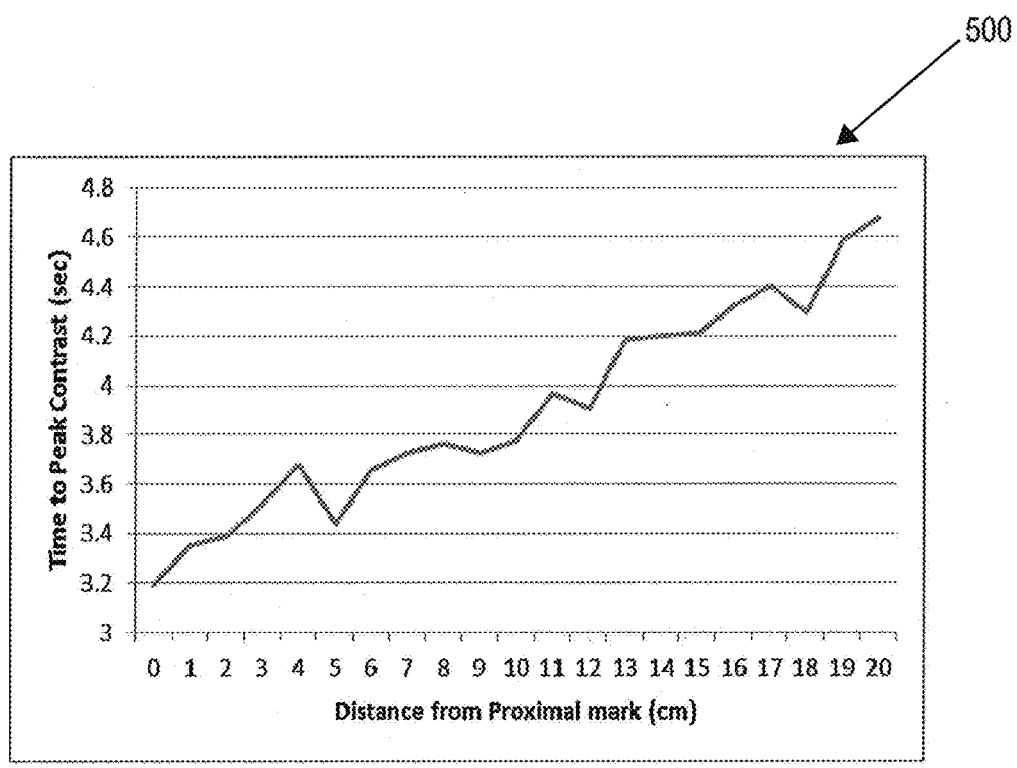
FIG. 5 is an exemplary graph illustrating time to peak contrast agent intensity, at points on a vessel of interest, versus distance of the points along the vessel of interest from a proximal point of the vessel of interest according to embodiments disclosed herein.

FIG. 5 is an exemplary graph 500 illustrating time (sec) to peak contrast agent intensity at points on a vessel of interest 302 versus distance (cm) of the points along the vessel of interest 302 from a proximal point 304 of the vessel of interest 302 according to embodiments disclosed herein.

According to an embodiment, a geodesic distance may be calculated by the processor(s) 121 as between a selected proximal point 304 and one of the points along a vessel of interest 302, such as the distal point 306, or points 308, 310, 312 along the vessel of interest 302, to determine the approximate distance that a contrast agent flows along the vessel of interest 302. The determined distance may be used for calculating the graph 500 as shown in FIG. 5.

According to an embodiment, the time encoded into the composite image 400 may be calculated by the processor(s) 121 to determine the time taken for a contrast agent to flow from a selected proximal point 304 to one of the points on the vessel of interest 302. As shown at step 212 illustrated in FIG. 2, the calculated graph 500 may be then provided by the processor(s) 121 to a terminal 130 for display to a user on the terminal 130, as shown in FIG. 5.

According to an embodiment, a time to peak contrast agent intensity at a point on the vessel of interest 302 may be computed by the processor(s) 121 using a weighted average or weighted median of time to peak contrast agent intensity at points surrounding the point on the vessel of interest 302. For the calculation of the weighted average or weighted median of time to peak contrast agent intensity at points surrounding the point on the vessel of interest 302, the processor(s) 121 may take into account an entire thickness of the vessel of interest 302. As a result, the effect of noise perturbing a single pixel in the processes medical images 300, forming the composite image 400, which may happen to coincide with a particular point on the vessel of interest 302, is lessened, if not diminished.

It is to be understood that embodiments of the present invention may be implemented in various forms of hardware, software, firmware, special purpose processes, or a combination thereof. In one embodiment, the present invention may be implemented in software as an application program tangible embodied on a computer readable program storage device. The application program may be uploaded to, and executed by, a machine comprising any suitable architecture. The system and method of the present disclosure may be implemented in a form of a software application running on a computer system, for example, a mainframe, a personal computer (PC), a handheld computer, a server, etc. The software application may be stored on a recording media locally accessible by the computer system or accessible via a hard wired or wireless connection to a network, for example, a local area network, or the Internet.

It is to be further understood that, because some of the constituent system components and method steps depicted in the accompanying figures may be implemented in software, actual connections between the systems components (or the process steps) may differ depending upon the manner in which the present invention is programmed Given the teachings of the present invention provided herein, one of ordinary skill in the related art may be able to contemplate these and similar implementations or configurations of the present invention.

While the present invention has been described in detail with reference to exemplary embodiments, those skilled in the art may appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

Although various embodiments that incorporate the teachings of the present invention have been shown and described in detail herein, those skilled in the art can readily devise many other varied embodiments that still incorporate these teachings. The invention is not limited in its application to the exemplary embodiment details of construction and the arrangement of components set forth in the description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

What is claimed is:

1. A method for tracking a blood flow within a vessel of a patient comprising:
    acquiring one or more medical images of the patient using an imaging system, the one or more images comprising at least one vessel of the patient;
    identifying a vessel of interest on the acquired one or more medical images, the vessel of interest containing a contrast agent;
    tracking the vessel of interest;
    generating a composite image from the acquired one or more medical images, the composite image comprising a time to peak contrast agent intensity at points on the vessel of interest; and
    calculating a graph comprising the time to peak contrast agent intensity at the points on the vessel of interest versus a distance of the points along the vessel of interest to identify an approximate distance that the contrast agent flows along the vessel of interest.

2. The method of claim 1, wherein the vessel of interest is identified by a user selection.

3. The method of claim 1, further comprising marking a proximal point on the vessel of interest.

4. The method of claim 1, further comprising marking a distal point on the vessel of interest.

5. The method of claim 1, wherein the distance of the points along the vessel of interest is determined by a geodesic distance of the points along the vessel of interest from a marked proximal point of the vessel of interest.

6. The method of claim 1, wherein the time to peak contrast agent intensity at the points is determined by a weighted average or weighted median of time to peak contrast agent intensity at selected points along the vessel of interest that surround the points on the vessel of interest.

7. The method of claim 1, further comprising correcting the tracking.

8. The method of claim 1, wherein the vessel of interest is tracked using a tracking algorithm.

9. The method of claim 1, wherein the composite image further comprises a value of the peak contrast agent intensity at the time on the points of the vessel of interest.

10. A non-transitory computer readable storage device comprising a computer program, the computer program when executed by a processor performing method steps comprising:
    identifying a vessel of interest on one or more medical images of a patient, the one or more medical images of the patient being acquired using an imaging system, the one or more images comprising at least one vessel of the patient, the vessel of interest containing a contrast agent;
    tracking the vessel of interest;
    generating a composite image from the acquired one or more medical images, the composite image comprising a time to peak contrast agent intensity at points on the vessel of interest; and
    calculating a graph comprising the time to peak contrast agent intensity at the points on the vessel of interest versus a distance of the points along the vessel of interest to identify an approximate distance that the contrast agent flows along the vessel of interest.

11. The non-transitory computer readable storage device comprising the computer program of claim 10, the computer program further performing marking a proximal point on the vessel of interest.

12. The non-transitory computer readable storage device comprising the computer program of claim 10, the computer program further performing marking a distal point on the vessel of interest.

13. The non-transitory computer readable storage device comprising the computer program of claim 10, the computer program further performing determining the distance of the points along the vessel of interest by a geodesic distance of the points along the vessel of interest from a marked proximal point of the vessel of interest.

14. The non-transitory computer readable storage device comprising the computer program of claim 10, the computer program further performing determining the time to peak contrast agent intensity at the points by a weighted average or weighted median of time to peak contrast agent intensity at selected points along the vessel of interest that surround the points on the vessel of interest.

15. The non-transitory computer readable storage device comprising the computer program of claim 10, the computer program further performing correcting the tracking.

16. The non-transitory computer readable storage device comprising the computer program of claim 10, the computer program performing tracking of the vessel of interest using a tracking algorithm.

17. The non-transitory computer readable storage device comprising the computer program of claim 10, wherein the composite image further comprises a value of the peak contrast agent intensity at the time on the points of the vessel of interest.

18. The method of claim 1, further comprising displaying at a terminal the one or more medical images, and/or the composite image, and/or the graph.

19. The method of claim 1, further comprising selecting the imaging system from the group consisting of: X-ray radiographs, MRI, CT, PET, PET-CT, SPECT, SPECT-CT, MR-PET, and 3D ultrasound.

\* \* \* \* \*